United States Patent
Schultz et al.

(10) Patent No.: US 7,371,912 B2
(45) Date of Patent: May 13, 2008

(54) PROCESS FOR MAKING XYLENE ISOMER USING A DEHEPTANIZER WITH A SIDE DRAW RECYCLE

(75) Inventors: Michael A. Schultz, Chicago, IL (US); Gregory F. Maher, Aurora, IL (US)

(73) Assignee: UOP LLC, Des Plaines, IL (US)

( * ) Notice: Subject to any disclaimer, the term of this patent is extended or adjusted under 35 U.S.C. 154(b) by 527 days.

(21) Appl. No.: 11/153,686

(22) Filed: Jun. 15, 2005

(65) Prior Publication Data

US 2006/0287563 A1  Dec. 21, 2006

(51) Int. Cl.
C07C 5/29 (2006.01)
(52) U.S. Cl. ..................... 585/478; 585/477
(58) Field of Classification Search ................ 585/478, 585/477
See application file for complete search history.

(56) References Cited

U.S. PATENT DOCUMENTS

| | | | |
|---|---|---|---|
| 3,700,744 A | 10/1972 | Berger et al. | 260/668 A |
| 4,697,039 A | 9/1987 | Schmidt | 585/477 |
| 6,395,950 B1 | 5/2002 | Rice | 585/738 |
| 6,472,578 B1 | 10/2002 | Rice | 585/804 |
| 6,483,002 B1 | 11/2002 | O'Brien | 585/826 |
| 6,540,907 B1 | 4/2003 | Towler et al. | 208/211 |
| 6,726,835 B2 | 4/2004 | Towler et al. | 208/211 |

*Primary Examiner*—Thuan Dinh Dang
(74) *Attorney, Agent, or Firm*—Maryann Maas

(57) ABSTRACT

In processes for recovering one or more xylene isomers and isomerizing the remaining isomers for recycle, the isomerate is distilled to provide a toluene-containing overhead, a mid-boiling fraction containing $C_8$ aromatics and a bottoms fraction containing $C_8$ aromatics and $C_9+$ aromatics. The mid-boiling fraction is recycled to the unit for recovering the sought xylene isomers and has sufficiently low content of $C_9+$ aromatics that the separation feed to the unit for recovering the sought xylene isomers contains up to about 500 ppm-mass $C_9+$ aromatics. The processes provide a high quality xylene isomer product while achieving at least one of debottlenecking, energy savings and capital savings.

17 Claims, 4 Drawing Sheets

PROCESS FOR MAKING XYLENE ISOMER USING A DEHEPTANIZER WITH A SIDE DRAW RECYCLE

FIELD OF THE INVENTION

This invention pertains to processes for making xylene isomer using a side draw from a deheptanizer distillation column to provide a high quality xylene isomer product while achieving at least one of debottlenecking, energy savings and capital savings.

BACKGROUND OF THE INVENTION

The xylenes, para-xylene, meta-xylene and ortho-xylene, are important intermediates which find wide and varied application in chemical syntheses. Para-xylene upon oxidation yields terephthalic acid which is used in the manufacture of synthetic textile fibers and resins. Meta-xylene is used in the manufacture of plasticizers, azo dyes, wood preservers, etc. Ortho-xylene is feedstock for phthalic anhydride production. See, for instance, Robert A. Meyers, HANDBOOK OF PETROLEUM REFINING PROCESSES, Second Edition, McGraw-Hill, 1997, Part 2, for a discussion regarding making xylenes.

Xylene isomers from catalytic reforming or other sources generally do not match demand proportions as chemical intermediates, and further comprise ethylbenzene which is difficult to separate or to convert. Para-xylene in particular is a major chemical intermediate. Adjustment of isomer ratio to demand can be effected by combining xylene-isomer recovery, such as adsorption for para-xylene recovery, with isomerization to yield an additional quantity of the desired isomer. Isomerization converts a non-equilibrium mixture of the xylene isomers which is lean in the desired xylene isomer to a mixture which approaches equilibrium concentrations. The isomerization results in by-products such as benzene, toluene and $C_9+$ aromatics being co-produced. In typical processes, the isomerate is distilled in a deheptanizer column to provide an overhead containing benzene and toluene and a bottoms stream containing para-xylene and other $C_8$ aromatics as well as $C_9+$ aromatics. The bottoms stream is passed to a xylene distillation column for separation of the $C_8$ aromatics from the $C_9+$ aromatics. The $C_8$ aromatics are passed to the xylene isomer recovery.

The feed to the xylene-isomer recovery must be highly free of $C_9+$ aromatics in order to meet product quality. Currently, the feed can contain no more than about 500 ppm-mass (mass parts per million) $C_9+$ hydrocarbons, and preferably less than about 100 ppm-mass 1,4-methylethylbenzene. Usually the xylene-containing feeds as well as the recycle from the deheptanizer column contain significant amounts of $C_9+$ hydrocarbons, e.g., often in excess of 2000, or even 3000, ppm-mass. Accordingly, a xylene column is used to separate these $C_9+$ hydrocarbons from the $C_8$ aromatics stream to be fed to the xylene-isomer recovery operation. Due to the proximity of the boiling points of $C_8$ aromatics and $C_9$ aromatics such as 1,4-methylethylbenzene, the xylene column can be quite large, often with over 90 theoretical plates, and involve a high reflux to feed ratio and thus substantial reboiler energy consumption.

Due to the large scale of commercial facilities to produce xylenes, especially para-xylene, even small improvements in capacity, capital costs or variable costs, such as reboiler energy consumption, can represent a material economic benefit to the xylene-isomer producer.

SUMMARY OF THE INVENTION

In accordance with this invention, processes for making xylene-isomers are provided in which a deheptanizer is used not only to separate benzene and toluene from a xylene-containing isomerate stream, but also to provide a mid-boiling fraction that can be recycled to a xylene-isomer recovery operation while still enabling the xylene product to meet commercial specifications. By so using the deheptanizer, one or more benefits can be obtained including the ability to debottleneck an existing facility, the ability to reduce reboiler energy consumption for the aggregate of xylene column and the deheptanizer, and the ability, in some instances, to eliminate the need for a xylene column.

In the broad aspects, the processes of this invention comprise: (a) separating at least one xylene isomer from a separation feed stream that contains para-xylene, ortho-xylene, meta-xylene and ethylbenzene and up to about 500 ppm-mass $C_9+$ aromatics, to provide a product fraction containing at least about 90 mass-percent of said at least one xylene isomer and a depleted fraction containing ethylbenzene, $C_9+$ aromatics and at least one other xylene isomer; (b) withdrawing at least a portion, preferably all, of the product fraction; (c) isomerizing at least a portion, preferably all, of the depleted fraction to provide an isomerate containing lower boiling, by-product hydrocarbons, para-xylene, meta-xylene, ortho-xylene, ethylbenzene and $C_9+$ aromatics; (d) fractionating by distillation at least a portion, preferably all, of the isomerate to provide a lower boiling fraction containing said lower boiling, by-product hydrocarbons and at least one mid-boiling fraction containing para-xylene, meta-xylene, ortho-xylene, ethylbenzene and $C_9+$ aromatics, and at least one higher boiling fraction containing para-xylene, meta-xylene, ortho-xylene, ethylbenzene and $C_9+$ aromatics wherein said at least one higher boiling fraction contains a greater mole percent of $C_9+$ aromatics than said at least one mid-boiling fraction, and preferably, at least about 10, say, about 10 to 90, more preferably 20 to 80, mass-percent of the total para-xylene, meta-xylene, ortho-xylene and ethylbenzene in the isomerate is contained in the mid-boiling fraction; (e) recycling at least a portion of said at least one mid-boiling fraction as a recycle stream to step (a); and (f) providing to step (a) at least one $C_8$ aromatic feed stream that contains between about 15 to 25 mass-percent para-xylene, ortho-xylene, meta-xylene and ethylbenzene and $C_9+$ aromatics, wherein the separation feed stream comprises the recycle stream of step (e) and the at least one $C_8$ aromatic feed stream.

In a preferred embodiment, at least one of the recycle stream of step (e) and at least one of the at least one $C_8$ aromatic feed stream of step (f) has greater than 500 ppm-mass of $C_9+$ aromatics, and at least one of the recycle stream of step (e) and at least one of the at least one $C_8$ aromatic feed stream of step (f) has less than 500 ppm-mass of $C_9+$ aromatics.

In one embodiment, the recycle stream of step (e) contains less than about 1500, say, about 500 or 700 to 1000, ppm-mass $C_9+$ aromatics, and the at least one aromatic feed stream contains up to about 500 ppm-mass $C_9+$ aromatics. In another embodiment, the recycle stream of step (e) contains less than about 500, say, between about 100 and 400, ppm-mass $C_9+$ aromatics. In this embodiment, the at least one $C_8$ aromatic feed stream may contain more or up to about 500 ppm-mass $C_9+$ aromatics, e.g., between about 100 and 1500, preferably between about 100 and 1200, ppm-mass $C_9+$ aromatics.

In another broad aspect of the processes of this invention, at least a portion of the $C_8$ aromatic feed stream is derived from the disproportionation of toluene where the disproportionation product is separated by distillation into at least one lower boiling toluene fraction, at least one higher boiling xylene-containing disproportionation fraction by distillation, and at least one mid-boiling disproportionation fraction containing para-xylene, meta-xylene, ortho-xylene, ethylbenzene and less than about 2500, preferably between about 500 and 1500, preferably 600 to 1200, ppm-mass $C_9$+ aromatics. In this aspect of the invention, the separation feed comprises at least a portion, preferably all, of the mid-boiling disproportionation fraction. In one more preferred embodiment of this aspect of the invention, the separation feed consists essentially of the mid-boiling disproportionation fraction and the recycle stream of step (e). Accordingly, no xylene column is required.

DETAILED DISCUSSION

The raw material for making xylenes is usually derived from naphtha or pygas. Normally, a raw material stream is subjected to pretreatments such as hydrotreating to remove sulfur and nitrogen compounds, and then the stream is subjected to reforming to generate aromatic compounds. The reforming is under sufficiently severe conditions that a wide range of aromatic compounds is produced including sought xylenes as well as benzene, toluene and $C_9$+ aromatics. The reformate is usually subjected to olefin saturation conditions. Lights such as butanes are removed by distillation, and higher molecular weight aliphatics are removed by extraction. The resulting aromatics-containing stream can be separated by distillation into various components. For instance, the $C_8$ aromatics (xylenes and ethylbenzene) can be fed to a xylene isomer recovery unit. Benzene may be recovered as a raw material for other petrochemical processes, and toluene can be subjected to disproportionation to generate $C_8$ aromatics and benzene. The generated $C_8$ aromatics can be used as feed to the xylene isomer recovery unit.

Figure 1:
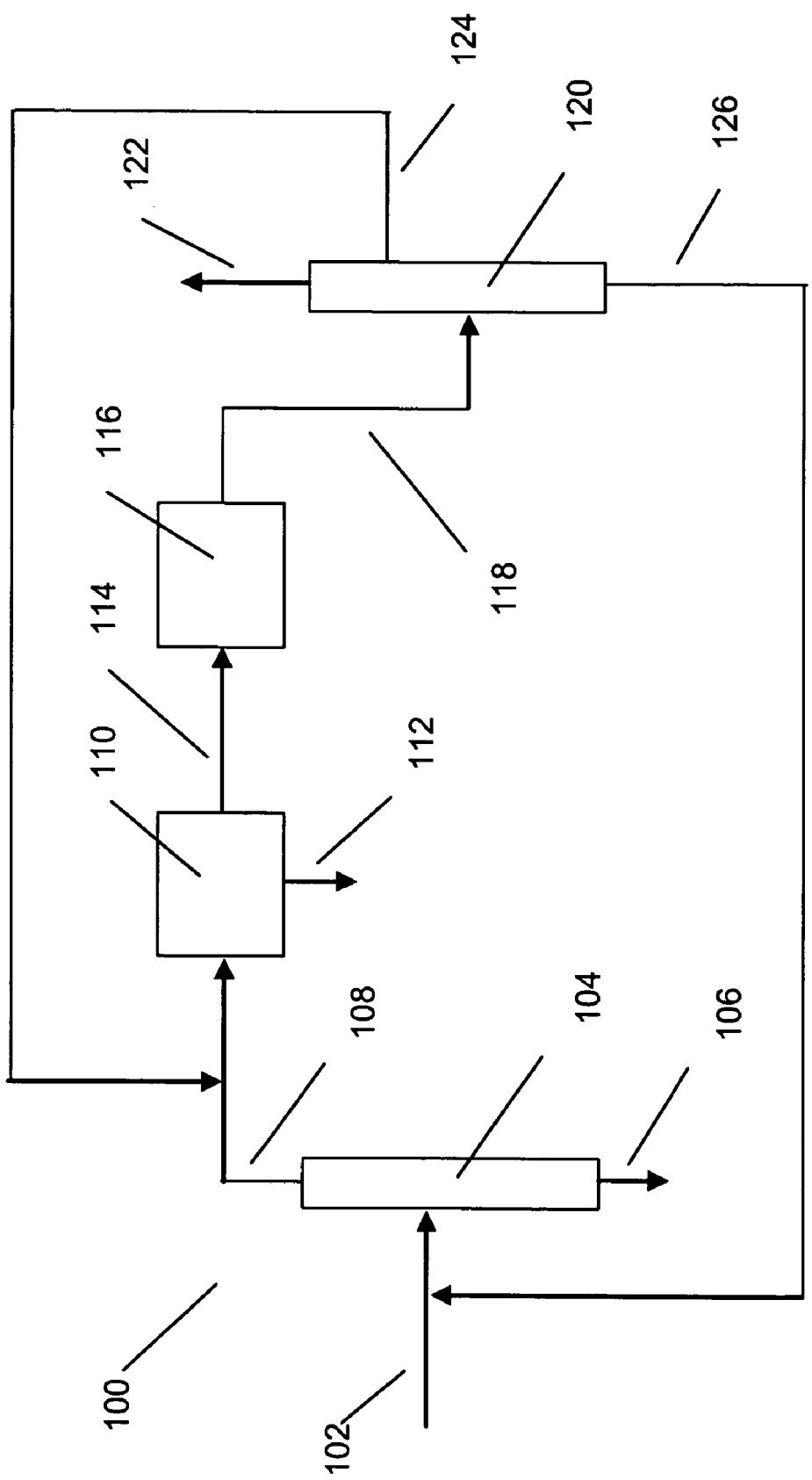
FIG. 1 is a schematic depiction of a process in accordance with the invention wherein a xylene column is used.

With reference to FIG. 1, apparatus 100 receives a $C_8$ aromatic feed stream via line 102 which is passed to xylene column 104. The $C_8$ aromatic feed stream is substantially devoid of toluene and lower boiling components but contains xylenes and ethylbenzene as well as $C_9$+ aromatics. Xylene column 104 is adapted via distillation to separate as an overhead, $C_8$ aromatics, and as a bottoms stream, $C_9$+ aromatics. If desired, the bottoms stream which is withdrawn via line 106, may be further separated into a $C_{9\ and\ 10}$-containing stream and a $C_{11+}$-containing stream, and the $C_{9\ and\ 10}$-containing stream can be subjected to transalkylation conditions to generate $C_8$ aromatics.

The overhead from xylene column 104 is passed via line 108 to xylene isomer recovery unit 110. The isomers having the greatest commercial value are ortho-xylene and especially para-xylene. Ortho-xylene can usually be recovered from the $C_8$ aromatics-containing stream fed to the xylene isomer recovery unit by distillation. Para-xylene is typically removed by either a sorption process or a crystallization process. Because of the nature of the downstream uses of para-xylene, the para-xylene product must meet stringent specifications, including for $C_9$+ aromatics. Whether the para-xylene recovery unit operation is sorption or crystallization, some $C_9$ aromatics, such as 1,4-methylethylbenzene are difficult to remove from para-xylene. Accordingly, the feed stream to the xylene isomer recovery unit (the separation feed) should contain up to about 500 ppm-mass $C_9$+ aromatics, and preferably should contain less than about 100 ppm-mass 1,4-methylethylbenzene. As shown, para-xylene is withdrawn from xylene isomer recovery unit 110 via line 112. The remaining xylene isomers and ethylbenzene pass from xylene recovery unit 110 to isomerization unit 116 via line 114.

Because the selective removal of one or more xylene isomers in xylene isomer recovery unit 110 results in a non-equilibrium xylene composition, the isomerization unit can serve to re-establish a near equilibrium composition of xylene isomers. The isomerization may also isomerize ethylbenzene, or, the ethylbenzene may be selectively dealkylated. Regardless of the type of isomerization, at least some $C_9$+ aromatics are generated. Often the isomerate contains between about 2000 and 10,000 ppm-mass $C_9$+ aromatics. Benzene toluene are also contained in the isomerate. Para-xylene is usually in an amount of about 20 to 25, more often about 21 to 23, mass-percent of total xylenes in the isomerate.

The isomerate passes via line 118 to deheptanizer distillation assembly 120. If desired, one or more intervening distillation columns may be used to remove lights and benzene such that the feed to deheptanizer distillation assembly 120 is substantially $C_7$+aromatics. Deheptanizer distillation assembly may be in one or more vessels, and may contain trays or structure packing or both. Deheptanizer distillation assembly 120 is adapted to provide an overhead containing toluene and benzene and any lighter components which is withdrawn via line 122, a mid-boiling fraction which is withdrawn via line 124 for recycle to xylene isomer recovery unit 110 to form part of the separation feed, and a bottoms fraction which is withdrawn via line 126 and recycled to xylene column 104.

The particular design of deheptanizer distillation assembly 120 will depend upon the sought amount of the mid-boiling fraction and the concentration of $C_9$+ aromatics that can be tolerated in the mid-boiling fraction such that the separation feed comprises up to about 500 ppm-mass of $C_9$+ aromatics. Usually deheptanizer distillation assembly 120 will comprise between about 15 and 70, more frequently, between about 20 and 60, theoretical distillation trays. With greater numbers of theoretical distillation trays, it is feasible to achieve lower concentration of $C_9$+ aromatics in the mid-boiling fraction. The processes of this invention may be operated such that the mid-boiling fraction contains greater than about 500 ppm-mass of $C_9$+ aromatics, and is admixed with the $C_8$ aromatic feed stream to provide a separation feed having up to about 500 ppm-mass $C_9$+ aromatics. In this mode of operation, the primary benefit of the processes of this invention is to reduce the load on the xylene column. Thus, the capacity of the xylene column to handle more fresh feed can be increased, thereby increasing the capacity of apparatus 100, or reducing the aggregate boiler energy requirements for xylene column 104 and deheptanizer distillation assembly 120. Normally in this mode of operation, the mid-boiling fraction will contain about 10 to 70 mass percent of the $C_8$ aromatics in the isomerate, and preferably between about 10 and 50 mass-percent of the $C_8$ aromatics in the isomerate. Due to the relative mass of the xylenes in the isomerate that will be recycled for xylene isomer recovery as compared to fresh feed introduced via line 102, which is usually at least about 2:1, say about 2.5:1 to 5:1, at higher concentrations of $C_9+$ aromatics, e.g., above about 750 ppm-mass, the amount of mid-boiling fraction that can be recycled while still meeting the separation feed $C_9+$ aromatics specification, is limited.

An alternative mode of operation is to provide a mid-boiling fraction from deheptanizer distillation assembly 120 that contains up to about 500 ppm-mass $C_9+$ aromatics. Not only can benefits of increasing the capacity of the xylene column and reducing aggregate reboiler energy consumption for the xylene column and the deheptanizer distillation assembly, be achieved, but also, potentials exist for capital saving. Where the $C_9+$ aromatics concentration is well below 500 ppm-mass, the mid-boiling fraction can be used to offset higher $C_9+$ aromatics concentrations in other components to the separation feed. Again, the higher mass of the xylenes in the isomerate to that in the fresh feed, enables the fresh feed to contain 750 or more ppm-mass $C_9+$ aromatics while still being able to achieve the $C_9+$ aromatics specification for the separation feed.

In this alternative mode of operation, the mid-boiling fraction typically contains at least about 10, preferably at least about 20, mass-percent of the xylenes in the isomerate. While the mid-boiling fraction can contain up to 90 or more mass percent of the xylenes in the isomerate, the size of the deheptanizer distillation assembly and aggregate reboiler energy requirements increase. Thus, often the mid-boiling fraction contains up to about 80 mass percent, and more preferably 25 to 75 mass-percent, of the xylenes in the isomerate.

The mid-boiling fraction is a side draw from deheptanizer distillation assembly 120. Where more than one distillation column is used such as is discussed below in conjunction with FIG. 2, the side draw can be the overhead from a second column. The side draw can be from a single distillation column. In such case, the composition of the mid-boiling fraction will be dependent upon the level in the column from which the draw is taken. A particularly beneficial design for deheptanizer distillation assembly 120 is a dividing wall column. See, for instance, the article appearing at page s14 of a SUPPLEMENT TO THE CHEMICAL ENGINEER, Aug. 27, 1992, and U.S. Pat. No. 4,230,533.

Figure 3:
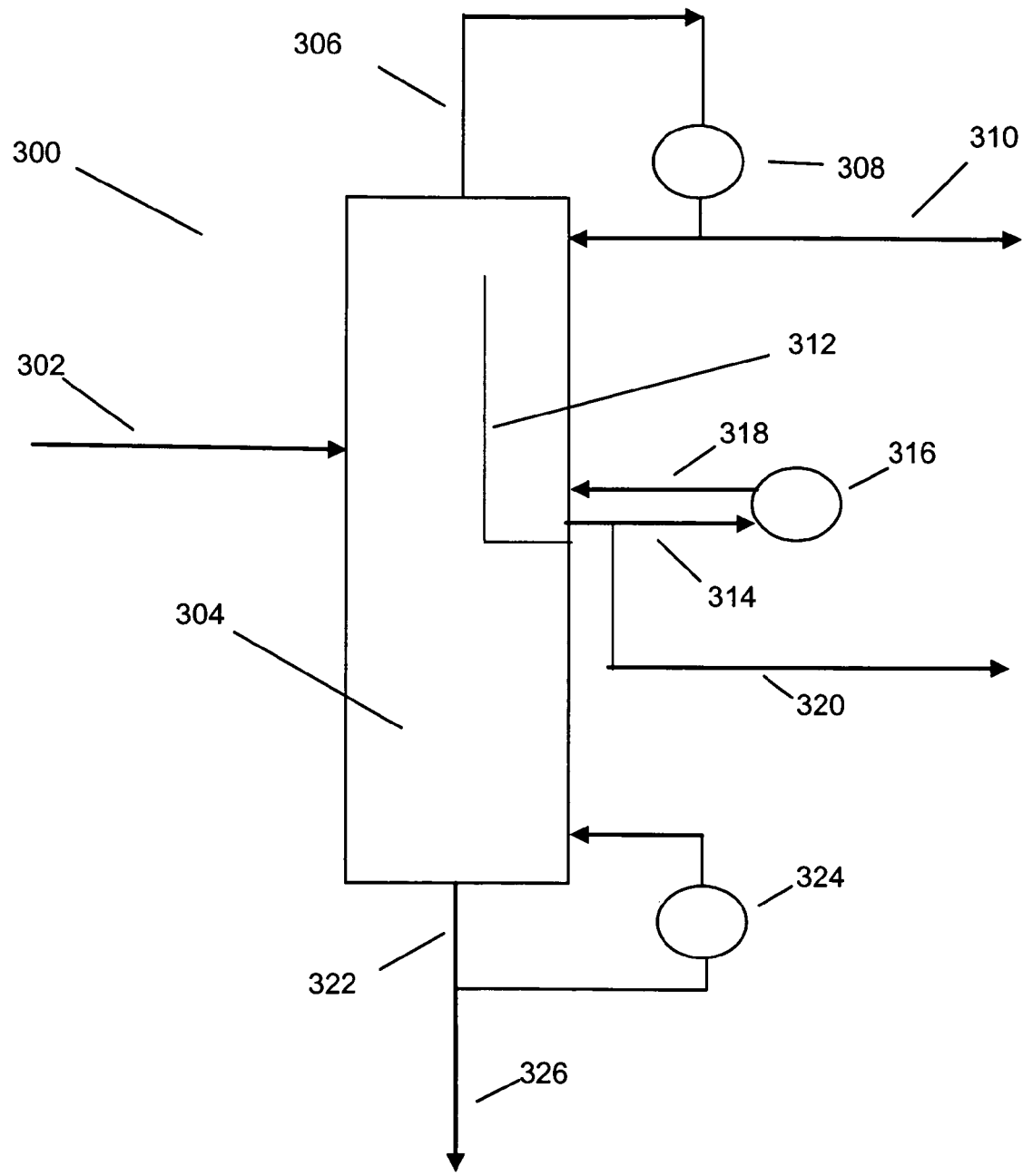
FIG. 3 is a schematic depiction of a dividing wall distillation assembly useful in the processes of this invention.
Figure 4:
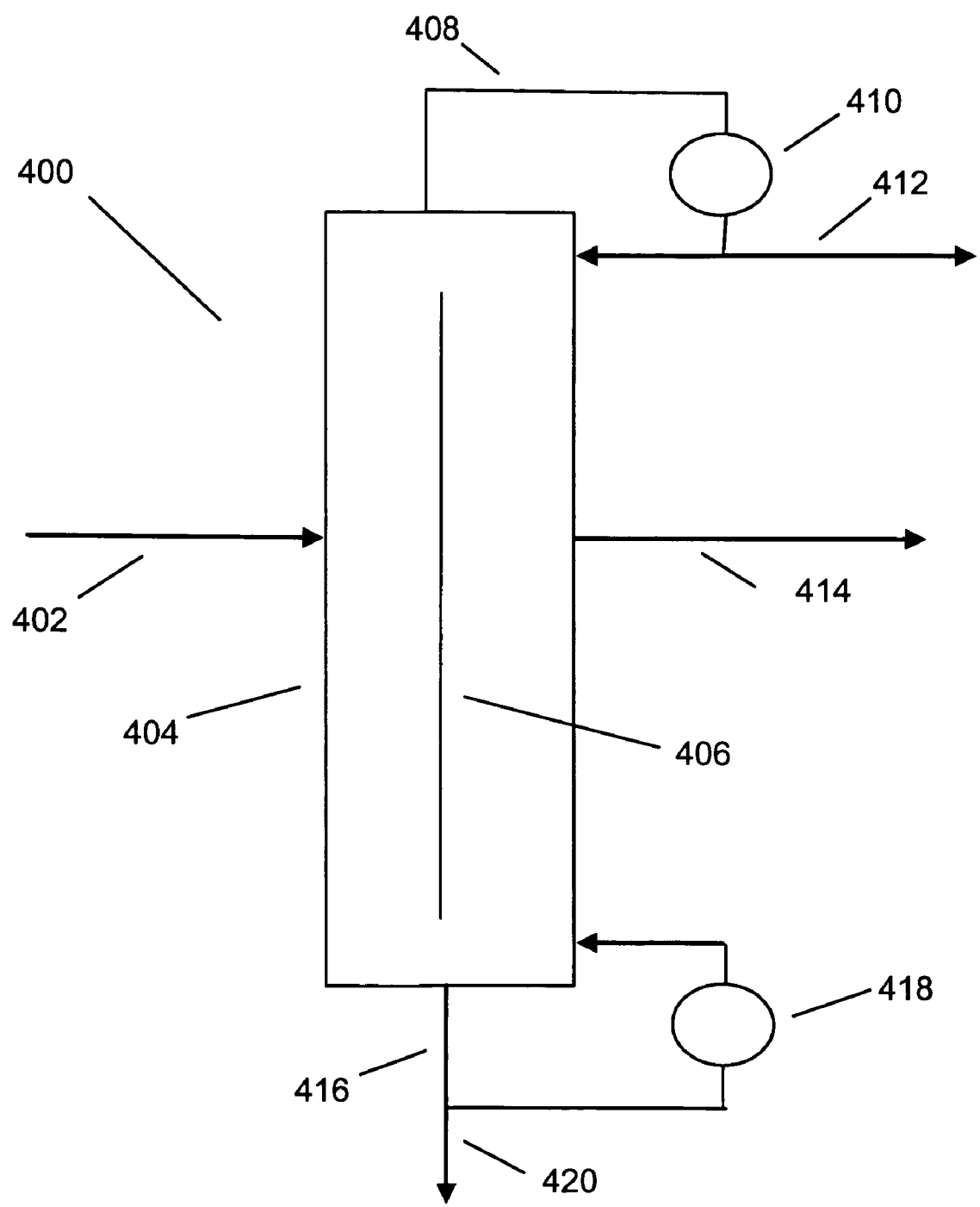
FIG. 4 is a schematic depiction of another type of dividing wall distillation assembly useful in the practice of this invention.

FIGS. 3 and 4 depict types of dividing wall distillation columns. In FIG. 3, distillation assembly 300 comprises feed inlet 302 to column 304. Overhead conduit at the tope of column 304 directs the vapor phase to condenser 308 for recycle as reflux to the top portion of distillation column 304. Conduit 310 is adapted to withdraw a portion of the condensate in line 308. Within column 304 is baffle 312 which is only open at its upper portion. Consequently, essentially only liquid phase enters the distillation zone defined by baffle 312. Hence, the concentration of $C_9+$ aromatics within this distillation zone will be less than that at the same height in the column outside this distillation zone. However, since essentially all the fluid in and outside this defined distillation zone is $C_6$ to $C_8$ aromatics, the temperature profiles in the defined zone and outside the zone, are substantially the same.

As shown, a bottoms stream is withdrawn from the defined zone vial line 314 and directed to reboiler 316 and returned to the zone via line 318. Line 320 is adapted to remove as the mid-boiling fraction, liquid phase in line 314.

Line 322 withdraws a bottoms stream from column 304, a portion of which is passed to line 326 and the remaining portion is passed through reboiler 324 and reintroduced into column 304.

FIG. 4 depicts another type of dividing wall distillation assembly 400. Conduit 402 is adapted to supply feed to column 404. Column 404 is provided with baffle 406 defining two distillation zones in column 404. Baffle 406 provides for fluid flow between the two sides of column 404 defined by baffle 406 only at the top and bottom of the column. Conduit 408 is adapted to withdraw vapor phase from the top of column 404 and pass it through condenser 410 with the resultant liquid being reintroduced as reflux to the top of column 404. A portion of the condensate is removed from conduit 408 via line 412.

Conduit 414 is provided on the side of column 404 for the purpose of withdrawing a side draw fraction. Conduit 414 is in communication with the zone defined by baffle 406 that is opposite the zone into which conduit 402 supplies feed. Conduit 416 is adapted to withdraw a bottoms liquid stream, pass it through reboiler 418 for reintroduction into the bottom portion of column 404. Conduit 420 is adapted to withdraw a portion of the bottoms stream from distillation assembly 400.

The following simulation data are provided to further illustrate the principles of the processes of this invention but are not in limitation thereof. Using a process such as described in connection with FIG. 1 but with an intervening distillation to remove benzene and lower boiling species, a feed as set forth below is introduced into deheptanizer distillation assembly 120:

| Component | Mass-percent |
|---|---|
| Toluene | 0.4 |
| Para-xylene | 18.2 |
| Ortho-xylene | 21.4 |
| Meta-xylene | 45.3 |
| Ethylbenzene | 7.8 |
| $C_9+$ aromatics | 3500 ppm-mass |
| Other | 6.7 |

Deheptanizer distillation assembly 120 has 32 theoretical distillation stages. A dividing wall column design is not used. A side draw is taken at stage 12. Table 1 summarizes the operation of the deheptanizer distillation assembly and the xylene column at various rates of side draw to provide a separation feed having 500 ppm-mass $C_9+$ aromatics.

TABLE 1

| Mass-percent total $C_8$ aromatics recovery in side draw | $C_9+$ aromatics in side draw, ppm-mol | $C_9+$ aromatics in bottoms, ppm-mol | Deheptanizer Reboiler Heat Requirement, calories per gram of para-xylene product | Xylene Column Reboiler Heat Requirement, calories per gram of para-xylene product |
|---|---|---|---|---|
| 0 | 0 | 3646 | 172 | 819 |
| 10 | 377 | 4020 | 174 | 776 |
| 20 | 695 | 4400 | 175 | 727 |

The use of a dividing wall column for the deheptanizer distillation assembly substantially increases the portion of the $C_8$ aromatics that can be recovered in the side draw while maintaining the $C_9+$ aromatics in the side draw below 500 ppm-mass. This principle is illustrated in connection with the following simulation.

Deheptanizer distillation assembly 120 comprises a dividing wall column as depicted in FIG. 4. The design of the deheptanizer distillation column and the xylene column are such that the separation feed contains 500 ppm-mass $C_9+$ aromatics, at different draws of mid-boiling fraction. The simulation is summarized in Table 2.

TABLE 2

| Mass-percent total $C_8$ aromatics recovery in side draw | Number of theoretical distillation stages in deheptanizer | Theoretical distillation stage at point of side draw in deheptanizer | Aggregate reboiler heat consumption for deheptanizer and xylene column, calories per gram of para-xylene product |
|---|---|---|---|
| 0 | 16 | none | 1050 |
| 25 | 19 | 15 | 990 |
| 50 | 23 | 11 | 960 |
| 75 | 25 | 8 | 920 |
| 99.5 | 50 | 8 | 1010 |

Figure 2:
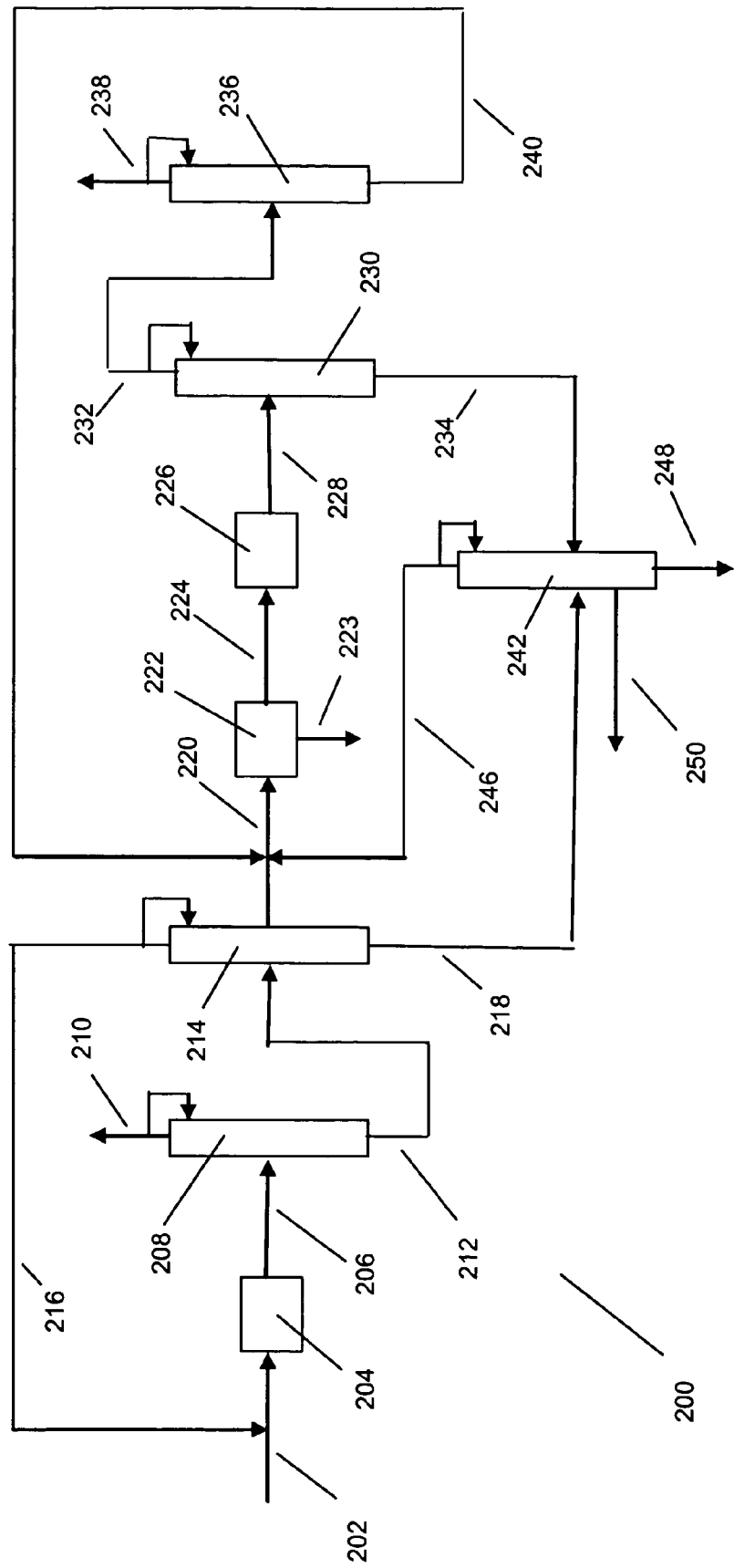
FIG. 2 is a schematic depiction of a process in accordance with the invention wherein no xylene column is used.

FIG. 2 depicts a para-xylene production facility 200 in which $C_8$ aromatics are generated by toluene disproportionation and the xylene column is eliminated. A toluene-containing feed is supplied by line 202 to disproportionation reactor 204 in which toluene is converted to $C_8$ aromatics and benzene. The disproportionation product is passed via line 206 to benzene distillation column 208 to provide a benzene-containing overhead that is withdrawn via line 210 and a xylene and toluene-containing bottoms stream that is directed by line 212 to toluene column 214.

Toluene column 214 may be in one or more vessels, and may contain trays or structure packing or both, and, preferably, is a dividing wall column. The overhead from toluene column is toluene which is recycled to disproportionation reactor 204 via line 216. Toluene column 214 is operated to provide a mid-boiling disproportionation fraction and a bottoms fraction. The bottoms fraction will contain $C_9+$ aromatics as well as some $C_8$ aromatics and is withdrawn via line 218. Typically the bottoms fraction is treated in a heavies distillation column to recover an additional portion of the $C_8$ aromatics and, if desired, $C_{9-10}$ aromatics for transalkylation to recover additional $C_8$ aromatics. The mid-boiling disproportionation fraction is withdrawn via line 220 and is subjected to xylene isomer recovery in xylene isomer recovery unit 222.

The particular design of toluene column will depend upon the sought amount of the mid-boiling disproportionation fraction and the concentration of $C_9+$ aromatics that can be tolerated such that the separation feed comprises up to about 500 ppm-mass of $C_9+$ aromatics. Usually toluene column will comprise between about 20 and 120, more frequently, between about 30 and 100, theoretical distillation trays. With greater numbers of theoretical distillation trays, it is feasible to achieve lower concentration of $C_9+$ aromatics in the mid-boiling disproportionation fraction as well as increase the relative amount of $C_8$ aromatics contained in the mid-boiling disproportionation fraction as opposed to the bottoms stream. The processes of this invention is usually operated such that the mid-boiling fraction contains greater than about 500 ppm-mass of $C_9+$ aromatics while the deheptanizer distillation assembly, as discussed later, is operated to provide up to about 500 ppm-mass $C_9+$ aromatics in its mid-boiling fraction. In some embodiments of the processes of this invention, the mid-boiling disproportionation fraction contains up to about 2500, preferably between about 700 and 2000, ppm-mass $C_9+$ aromatics. Normally the mid-boiling disproportionation fraction will contain at least about 40, preferably between about 50 and 99, mass percent of the $C_8$ aromatics in the disproportionation product.

The xylene isomer recovery unit may be the same as described in conjunction with FIG. 1. As depicted, a para-xylene product stream is withdrawn via line 223. The remaining xylene isomers and ethylbenzene pass from xylene recovery unit 222 to isomerization unit 226 via line 224.

Because the selective removal of one or more xylene isomers in xylene isomer recovery unit 222 results in a non-equilibrium xylene composition, the isomerization unit can serve to re-establish a near equilibrium composition of xylene isomers. The isomerization may also isomerize ethylbenzene, or, the ethylbenzene may be selectively dealkylated. Regardless of the type of isomerization, at least some $C_9+$ aromatics are generated. Often the isomerate contains between about 2000 and 10,000 ppm-mass $C_9+$ aromatics. Benzene and toluene are also contained in the isomerate. Para-xylene is usually in an amount of about 20 to 25, more often about 21 to 23, mass-percent of total xylenes in the isomerate.

The isomerate passes via line 228 to a deheptanizer distillation assembly which employs two distillation columns, 230 and 236. If desired, one or more intervening distillation columns may be used to remove lights and benzene such that the feed to deheptanizer distillation assembly 230 is substantially $C_7+$aromatics. As discussed in connection with FIG. 1, deheptanizer distillation assembly may be in one vessel, may be a dividing wall column, and may contain trays or structure packing or both.

Column 230 is adapted to provide an overhead containing $C_8$ aromatics, toluene and benzene which is passed via line 232 to column 236. The bottoms in column 230 will contain $C_9+$ aromatics as well as some of the $C_8$ aromatics and is passed via line 234 to heavies column 242.

Distillation column 236 provides an overhead containing toluene and lower boiling components that is withdrawn via line 238. The bottoms fraction contains $C_8$ aromatics and is recycled via line 240 to xylene isomer recovery unit 222.

As stated above, the particular design of deheptanizer distillation assembly 120 will depend upon the sought amount of the mid-boiling fraction and the concentration of $C_9+$ aromatics that can be tolerated in the mid-boiling fraction such that the separation feed comprises up to about 500 ppm-mass of $C_9+$ aromatics. Usually deheptanizer distillation assembly will comprise between about 15 and 70, more frequently, between about 20 and 60, theoretical distillation trays. With greater numbers of theoretical distillation trays, it is feasible to achieve lower concentration of $C_9+$ aromatics in the mid-boiling fraction. In the embodiment of this invention where the xylene column is eliminated, the deheptanizer assembly is operated such that the mid-boiling fraction contains less than about 500, preferably less than about 400, say 100 to 400, ppm-mass of $C_9+$ aromatics. Normally in this mode of operation, the mid-boiling fraction will contain at least about 30, preferably between about 60 to 99 mass percent of the $C_8$ aromatics in the isomerate. The relative mass of the xylenes in the isomerate that will be recycled for xylene isomer recovery as compared to the mid-boiling disproportionation fraction introduced via line 220 is usually at least about 2:1, say about 2.5:1 to 5:1.

Returning to heavies distillation column 242, as depicted, the bottoms stream from toluene column 214 is also a feed.

The overhead contains $C_8$ aromatics and can be directed to xylene isomer recovery unit 222 via line 246. A bottoms fraction which contains heavy aromatics, e.g., $C_{10+}$, is withdrawn via line 248. In preferred aspects of the processes of this invention, less than about 0.5, preferably less than 0.2, mass-percent of the $C_8$ aromatics contained in the disproportionation product is contained in this bottoms fraction. As shown, a side draw is taken via line 250 from heavies column 242 and is $C_{9\ and\ 10}$-containing stream that may be used for transalkylation.

The following simulation is provided to further illustrate the principles of this aspect of the invention. For this simulation, dividing wall columns such as depicted in FIG. 4 are used for both the toluene column and the deheptanizer distillation assembly. The feed composition to the toluene column is:

| Component | Mass-percent |
|---|---|
| Toluene | 27.8 |
| $C_8$ aromatics | 38.4 |
| $C_9$+ aromatics | 0.328 |
| Other | 0.9 |

The feed composition to the deheptanizer distillation assembly is:

| Component | Mass-percent |
|---|---|
| Toluene | 0.4 |
| Para-xylene | 7.8 |
| Ortho-xylene | 21.4 |
| Meta-xylene | 45.3 |
| Ethylbenzene | 7.8 |
| $C_9$+ aromatics | 3500 ppm-mass |
| Other | 6.7 |

The total feed to xylene isomer recovery unit contains 500 ppm-mass $C_9$+ aromatics, and the mass ratio of the mid-boiling fraction from the deheptanizer distillation assembly to mid-boiling disproportionation fraction from the toluene fraction is about 3:1. Table 3 summarizes the simulation of this embodiment without a xylene column with a typical process using a xylene column and no side draws on either the toluene column or the deheptanizer distillation assembly. The aggregate reboiler heat is for the xylene column (if used), and the toluene column and deheptanizer distillation assembly.

TABLE 3

| | Xylene Column, theoretical Stages | Deheptanizer, theoretical stages (stage of side draw) | Deheptanizer side draw $C_9$+ aromatics, ppm-mass | Toluene column, theoretical stages (stage of side draw) | Toluene column side draw $C_9$+ aromatics, ppm-mass | Aggregate reboiler heat, calories per gram of para-xylene product |
|---|---|---|---|---|---|---|
| Base case | 94 | 16 (0) | n/a | 30(0) | n/a | 1347 |
| Invention | None | 54 (12) | 274 | 95(26) | 1000 | 1206 |

What is claimed is:

1. A process for making xylene isomer comprising:
   (a) separating at least one xylene isomer from a separation feed stream that contains para-xylene, ortho-xylene, meta-xylene and ethylbenzene and up to about 500 ppm-mass $C_9$+ aromatics, to provide a product fraction containing at least about 90 mass-percent of said at least one xylene isomer and a depleted fraction containing ethylbenzene, $C_9$+ aromatics and at least one other xylene isomer;
   (b) withdrawing at least a portion of the product fraction;
   (c) isomerizing at least a portion of the depleted fraction to provide an isomerate containing lower boiling, by-product hydrocarbons, para-xylene, meta-xylene, ortho-xylene, ethylbenzene and $C_9$+ aromatics;
   (d) fractionating by distillation at least a portion of the isomerate to provide a lower boiling fraction containing said lower boiling, by-product hydrocarbons and at least one mid-boiling fraction containing para-xylene, meta-xylene, ortho-xylene, ethylbenzene and $C_9$+ aromatics, and at least one higher boiling fraction containing para-xylene, meta-xylene, ortho-xylene, ethylbenzene and $C_9$+ aromatics wherein said at least one higher boiling fraction contains a greater mole percent of $C_9$+ aromatics than said at least one mid-boiling fraction;
   (e) recycling at least a portion of said at least one mid-boiling fraction as a recycle stream to step (a); and
   (f) providing to step (a) at least one $C_8$ aromatic feed stream that contains between about 15 to 25 mass-percent para-xylene, ortho-xylene, meta-xylene and ethylbenzene and $C_9$+ aromatics,
wherein the separation feed stream comprises the recycle stream of step (e) and the at least one $C_8$ aromatic feed stream.

2. The process of claim 1 wherein at least about 10 mass-percent of the total para-xylene, meta-xylene, ortho-xylene and ethylbenzene in the isomerate is contained in the mid-boiling fraction.

3. The process of claim 2 wherein the recycle stream of step (e) contains less than about 1500 ppm-mass $C_9$+ aromatics, and the at least one aromatic feed stream contains up to about 500 ppm-mass $C_9$+ aromatics.

4. The process of claim 2 wherein the recycle stream of step (e) contains less than about 500 ppm-mass $C_9$+ aromatics, and at least one $C_8$ aromatic feed stream contains more than about 500 ppm-mass $C_9$+ aromatics.

5. The process of claim 2 wherein the fractionating of step (d) is by a dividing wall distillation column.

6. The process of claim 1 wherein at least one at least one $C_8$ aromatic feed stream is obtained by a distillation to separate $C_8$ aromatics from $C_9$+ aromatics, and at least one higher boiling fraction from the distillation of step (d) is fed to the distillation.

7. The process of claim 1 wherein at least a portion of the $C_8$ aromatic feed stream is derived from the disproportionation of toluene where the disproportionation product is fractionated by distillation into at least one lower boiling toluene fraction, at least one higher boiling xylene-containing disproportionation fraction, and at least one mid-boiling disproportionation fraction containing para-xylene, meta-xylene, ortho-xylene, ethylbenzene and less than about 2500 ppm-mass $C_9+$ aromatics, and at least a portion of the mid-boiling disproportionation fraction is passed to step (a).

8. The process of claim 7 wherein the distillation of the disproportionation product is by a dividing wall column.

9. The process of claim 7 wherein the recycle stream of step (e) contains less than about 500 ppm-mass $C_9+$ aromatics.

10. The process of claim 7 wherein the separation feed consists essentially of the mid-boiling disproportionation fraction and the recycle stream of step (e).

11. A process for making xylene isomer comprising:
(a) separating at least one xylene isomer from a separation feed stream that contains para-xylene, ortho-xylene, meta-xylene and ethylbenzene and up to about 500 ppm-mass $C_9+$ aromatics, to provide a product fraction containing at least about 90 mass-percent of said at least one xylene isomer and a depleted fraction containing ethylbenzene, $C_9+$ aromatics and at least one other xylene isomer;
(b) withdrawing at least a portion of the product fraction;
(c) isomerizing at least a portion of the depleted fraction to provide an isomerate containing lower boiling, by-product hydrocarbons, para-xylene, meta-xylene, ortho-xylene, ethylbenzene and $C_9+$ aromatics;
(d) fractionating by distillation at least a portion of the isomerate to provide a lower boiling fraction containing said lower boiling, by-product hydrocarbons and at least one higher boiling fraction containing para-xylene, meta-xylene, ortho-xylene, ethylbenzene and $C_9+$ aromatics;
(e) fractionating by distilling at least a portion of said at least one higher boiling fraction to provide a xylene fraction containing para-xylene, meta-xylene, ortho-xylene, ethylbenzene and up to about 500 ppm-mass $C_9+$ aromatics;
(f) providing to step (a) at least a portion of said xylene fraction;
(g) disproportionating toluene to provide a disproportionation product;
(h) fractionating by distillation said disproportionation product into at least one $C_8$ aromatic feed stream that contains between about 15 to 25 mass-percent para-xylene, ortho-xylene, meta-xylene and ethylbenzene and $C_9+$ aromatics, into at least one lower boiling toluene fraction, at least one higher boiling xylene-containing disproportionation fraction by distillation, and at least one mid-boiling disproportionation fraction containing para-xylene, meta-xylene, ortho-xylene, ethylbenzene and less than about 2500 ppm-mass $C_9+$ aromatics; and
(i) passing at least a portion of said at least one mid-boiling disproportionation fraction to step (a) or step (e).

12. The process of claim 11 wherein the at least one mid-boiling disproportionation fraction contains between about 500 and 1500 ppm-mass $C_9+$ aromatics.

13. The process of claim 11 wherein at least one mid-boiling disproportionation fraction is passed to step (a).

14. The process of claim 11 wherein at least one mid-boiling disproportionation fraction is passed to step (b).

15. The process of claim 11 wherein the fractionation of step (d) provides at least one mid-boiling fraction containing para-xylene, meta-xylene, ortho-xylene, ethylbenzene and $C_9+$ aromatics, that is lower boiling than at least one higher boiling fraction, and said at least one higher boiling fraction contains a greater mole percent of $C_9+$ aromatics than said at least one mid-boiling fraction; and at least a portion of said at least one mid-boiling fraction is recycled to step (a).

16. The process of claim 15 wherein said at least one mid-boiling fraction contains less than about 500 ppm-mass $C_9+$ aromatics.

17. The process of claim 16 wherein at least a portion of said at least one mid-boiling disproportionation fraction is passed to step (a).

\* \* \* \* \*